(12) United States Patent
Brookshire

(10) Patent No.: US 8,323,703 B2
(45) Date of Patent: Dec. 4, 2012

(54) STORABLE, CONSUMABLE PRE-NASCENT IODINE

(76) Inventor: John Staley Brookshire, Bedford, TX (US)

( * ) Notice: Subject to any disclaimer, the term of this patent is extended or adjusted under 35 U.S.C. 154(b) by 1301 days.

(21) Appl. No.: 11/515,530

(22) Filed: Sep. 5, 2006

(65) Prior Publication Data

US 2009/0022816 A1   Jan. 22, 2009

Related U.S. Application Data

(60) Provisional application No. 60/714,331, filed on Sep. 6, 2005.

(51) Int. Cl.
*A01N 59/12* (2006.01)
*A61K 33/18* (2006.01)

(52) U.S. Cl. .................................. 424/667; 205/687

(58) Field of Classification Search ..................... None
See application file for complete search history.

(56) References Cited

U.S. PATENT DOCUMENTS 1,889,195 A * 11/1932 Engels .......................... 424/667

OTHER PUBLICATIONS

McMillin, A Review of Cayce-Based Energy Medicine for Chonic Neurologic Disease, &th Annual Cayce Health Professionals Symposium (Sep. 15, 2002), p. 1-8.*
How to Make Atomidine, Minnesota Wellness Publications, Inc. (2006), pp. 1-4.*

* cited by examiner

*Primary Examiner* — James H Alstrum Acevedo
*Assistant Examiner* — Frank Choi
(74) *Attorney, Agent, or Firm* — Charles D. Gunter, Jr.

(57) ABSTRACT

This discovery is storable, pre-nascent iodine that activates and: produces nascent iodine over a two-to-three-hour period within the body when diluted in water and consumed. The iodine is in a low concentration in a tincture of grain alcohol. A quantity of tincture is submerged in a glass container in an electrolytic bath between two electrodes and subjected to a specific amperage for a period of time. This action causes the diatomic bond of the iodine molecule to be broken with the iodine atom receiving excitation energy from the magnetic field. When diluted and consumed into the body, the nascent iodine is able to produce significant beneficial effects in the body.

4 Claims, 1 Drawing Sheet

Storable, consumable pre-nascent iodine
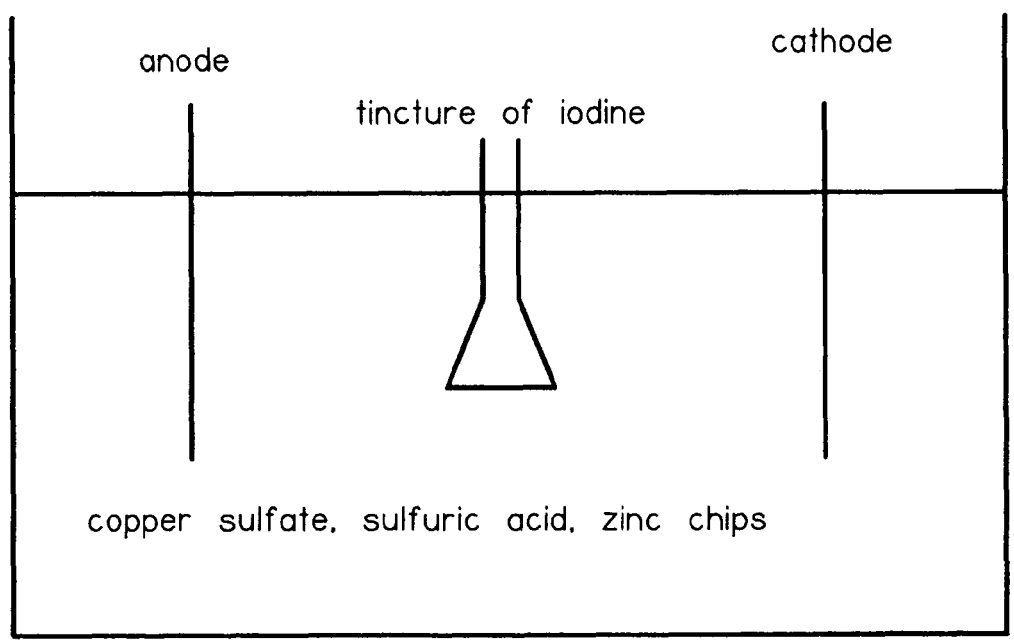

STORABLE, CONSUMABLE PRE-NASCENT IODINE

CROSS-REFERENCE TO RELATED APPLICATIONS

This application claims priority of the filing date of provisional patent application U.S. 60/714,331, filed Sep. 6, 2005.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

This invention relates to storable, consumable, nascent iodine in a tincture which is used as an iodine supplement. It has sufficient iodine in an electromagnetically excited state to be active in the body for 2 to 3 hours as elemental iodine.

2. Description of Related Art Including Information Disclosed Under 37 CFR 1.97 and 1.98

Nascent iodine is a well-known anti-infective agent as well as a vital component of T3 and T4 hormone production within the body. Attempts to find an effective method for ingesting nascent iodine began with the use of Brown Iodide of Lime, as a loose combination of iodine and calcium oxide, which sets nascent iodine free when taken into the stomach, originated by Nichols (*A Practitioner's Handbook Of Materia Medica And Therapeutics Based Upon Established Physiological Actions* by Thomas S. Blair, M.D., 1907.) This was not a very effective method even at that time.

Today there are several patents utilizing nascent iodine as the primary factor. One set of patents (U.S. Pat. No. 6,838,050 and U.S. Pat. No. 6,482,309) refers to the electrolytic generation of nascent iodine as a method of treatment for the prevention of infections associated with medical implant devices. Another patent (U.S. Pat. No. 5,232,914) relates to the use of nascent iodine in a solid germicidal, pre-iodine composition. Still another (U.S. Pat. No. 6,592,890) refers to use of nascent iodine in a wound dressing. And the last relevant patent (U.S. Pat. No. 5,538,740) refers to the therapeutic and cosmetic compositions involving nascent iodine for the treatment of skin. None of the above patents involve a consumable form of nascent iodine.

In 1912 Sunkar A. Bisey developed a Westernized form of nascent iodine. This formula was in a saline solution, based upon traditional medicines from India. This traditional medicine was utilized to treat fevers, malaria, and other illnesses, and was produced primarily from seaweed. No patent for Bisey's product has been located, (although Bisey had several patents.) However, information obtained from Schieffelin and Company indicates that this formula was highly utilized by physicians and hospitals from 1926 until Bisey's death in 1935. Promotional claims by Schieffelin stated that this saline/iodine solution was active in the nascent state when dissolved in water and consumed (Druggist's circular titled "Atomidine in Medicine", distributed by Schieffelin & Co. Mount Vernon, N.Y.). This circular refers to the 1930's product only. Although no record was found of the exact composition of the saline solution (other than the iodine portion), information was obtained about a process which was utilized to produce this form of nascent iodine. Indications were that Bisey's solution was water-based, as opposed to alcohol-based.

In October 1931, Dr. Sunkar A. Bisey met with Edgar Cayce of Virginia Beach, Va., and an investor interested in Bisey's nascent iodine product. Edgar Cayce suggested a change in the method of production, and this new method of production formed the basis for a saline iodine solution which Bisey used for the last four years of his life. A tincture of iodine solution has obvious differences with a saline solution, but both producing nascent iodine indicate there should be similar characteristics. After Bisey's death in 1935, the use of his product seems to have declined then disappeared.

There are two companies that claim to produce the Bisey product today, but both are based on iodine trichloride and have never claimed to present nascent iodine to the body system; in fact, one even warns against internal use. Both companies hold their production methods in secret; all that is known is that the products are 1% iodine trichloride, which is considered toxic in quantities larger than a few drops.

In the late 1990's Phillip Thomas of Altamonte Springs, Fla., experimented with a 1% tincture of iodine and achieved a product he called Rejuvidine. It was produced by a method similar to Sunkar A. Bisey's product. It provided a significant step forward as a health supplement, but due to several factors, the product did not achieve a sufficient energy level to attain the nascent state of iodine in useful quantity.

Due to the nature of iodine and the fear of iodine toxicity, it is essential that as much of the iodine be in a nascent state as possible because the human body should not just consume more and more iodine at a time to gain the nascent iodine benefit. Hence, a method to achieve a high quantity of nascent state iodine is desired.

The need for a safe iodine supplement has never been greater according to those researching iodine deficiencies. Dr. David Brownstein, author of *Iodine Why You Need It, Why You Can't Live Without It*, reports that 95% of his patients tested have demonstrated low iodine levels.

BRIEF SUMMARY OF THE INVENTION

A tincture of iodine solution being formed may include the step of preparing a predetermined quantity of the iodine and raising an energy level of the predetermined quantity of iodine to produce nascent iodine level to make it useful to the body.

The nascent iodine level may become activated when diluted in water and consumed, and the nascent iodine may form within the body as the iodine gradually loses energy (relaxes) when diluted.

The nascent iodine may perform anti-infective activity, and the nascent iodine may produce T3 and T4 hormones within the thyroid.

The nascent iodine may be adaptable to fight parasites including malaria, dengue, and black-water fever within the body, and the nascent iodine may be adaptable to fight gastro-intestinal disorders.

The nascent iodine may be adaptable to reduce blood pressure, and the nascent iodine may be adaptable to treat iodine deficiency diseases.

The nascent iodine may be adaptable to treat sinusitis, bronchitis, and asthma, and step of raising the energy level may include breaking the diatomic bond of the iodine.

The step of raising the energy level may include subjecting the iodine to a magnetic field.

BRIEF DESCRIPTION OF THE DRAWING

FIG. 1 illustrates the method for producing pre-nascent iodine for health applications.

DETAILED DESCRIPTION OF THE INVENTION

Brief Summary:

A storable, consumable form of nascent iodine that is effective in a safe quantity (a few drops) and yet has a strong nascent iodine component, promoting increased energy and improved health as a general health supplement. An electromagnetic field is used to produce the breaking of the diatomic bond of the iodine molecule through magnetic excitation. Tincture of iodine is an excellent medium for containing this state of pre-nascent iodine until diluted in water and consumed. Other forms of production with continuous flowing tincture solution and using direct magnetic fields can be devised for industrial production.

The body can utilize iodine in the nascent state in a natural way since the nascent state of iodine is generated within the thyroid in order to produce T3 and T4 hormones.

Supplementing the diet with iodide or iodine is known to boost the immune system. The addition of iodine in the nascent state with its well-documented anti-infective effect will complement this health benefit in the body.

It is submitted at this time only as a health supplement.

Detailed Description:

In order to be of full benefit, the energy level had to be increased in the tincture of iodine, since there is an obvious limit to the quantity of iodine safe to consume. The Rejuvidine (made by Phillip Thomas) is produced (16 ounces of tincture of iodine) by submerging it in an electrolytic bath of 3 gallons of maker solution (bath) for five minutes at a resistance of 10 amp of AC current. After repeated requests to have the nascent activity increased by modifications of the procedures, Phillip Thomas stated he had no interest in changing his process, that he had many happy customers as it is.

My process is different from his in the following ways: amperage was increased from 10 amps to 30 amps; quantity of tincture being energized was decreased from 16 ounces to eight ounces while the maker solution (electrolytic solution) was increased from 3 gallons to 8 gallons, and the time was increased from 5 minutes to 20 minutes. This level of activity is sufficient to break the diatomic bond of the iodine and elevate the iodine atom into the elemental state.

The resulting iodine has sufficient nascent-reacting elemental iodine to give the desired effect for 2-3 hours using only a few drops dissolved in water and consumed. This quantity of nascent iodine required to have beneficial effects is similar to that quantity of iodine required to purify water for drinking in many areas of the world.

The simplest way to produce the nascent-reacting iodine is to prepare a tincture of iodine, for example 1% iodine by weight in grain alcohol. Prepare an electrolytic bath of copper sulfate, sulfuric acid and zinc chips. (An effective electrolytic solution is $2/3$ lb of copper sulfate per gal., $1/2$ ounce of sulfuric acid per gal. and $1/3$ ounce of zinc chips per gal.) Place anodes of copper and of nickel alloy ($1/2$ inch diameter and 14 inches long) attached to an AC current on either side of a glass container, with the tincture of iodine, submerged in the electrolytic bath. The AC current is run at 30 amps of resistance for 20 minutes. The volume of tincture of iodine in ounces should not exceed the gallons of the electrolytic solution. The container for the electrolytic solution should be glass or ceramic.

The nascent-reacting iodine should be stored in a dark glass container at a cool temperature and out of direct light. It is most effective when consumed directly after mixing a few drops with at least 2 to 3 ounces of water and taken on an empty stomach.

Description of Steps to Produce:

The following is considered the best mode for making 8 ounces of nascent iodine.

1. A glass or ceramic container of sufficient size is filled with 8 gallons of distilled water, allowing for a few inches of clearance between the top of the water and top of the container.

2. An electrolytic solution is made using $5 1/3$ lb of copper sulfate, 4 ounce of sulfuric acid and $2 2/3$ ounce of zinc chips. It is prepared by adding in this order, these chemicals and mixing for approximately 20 minutes.

3. A $1/2$ inch diameter copper rod of 14 inch length to function as an anode is attached to the one side of the container. A similar size nickel rod is attached to the opposite side of the container as the other anode. The amperage can be adjusted to the necessary 30 amps by adjusting the depth these rods go into the electrolytic solution.

4. A long necked glass flask with a glass stopper containing no more than 8 ounces of 1% tincture of iodine made from grain alcohol is lowered into the center of the container so that the electrical current flow between the two anodes passes around the flask.

5. Using safe electrical procedures connect a 110 AC current to flow through the anodes across the electrolytic solution for 20 minutes.

6. The tincture of iodine is now in the pre-nascent state and should be stored in a dark glass bottle until ready for use.

7. A typical use as a health supplement might be 5 drops in a half glass (4 ounces) of water. It is most effective taken on an empty stomach. It will be effective in the body in the nascent state for up to two or three hours as the excitation energy from the electromagnetic field relaxes. Consumable nascent iodine has been provided the body with only 5 drops of 1% tincture of iodine, less iodine than would be used to purify a glass of water on a camping trip.

I claim:

1. A method of manufacturing consumable pre-nascent iodine, the method comprising the steps of:

providing a given quantity of tincture of iodine solution, the iodine in the tincture of iodine solution being in the form of diatomically bonded iodine molecules;

subjecting the diatomically bonded iodine molecules in the tincture of iodine solution to an electromagnetic field by submerging a container of the tincture of iodine solution in an electrolytic bath between electrodes, the container being subjected to a predetermined current density for a predetermined period of time, the current density being sufficient to decompose the diatomically bonded iodine molecules into elemental, pre-nascent iodine, the elemental, pre-nascent iodine being present in the solution in a concentration sufficient to make it useful to a human body;

wherein a glass container containing 8 ounces of a tincture of iodine solution is submerged in an 8 gallon electrolytic bath, the tincture of iodine solution containing 1% diatomically bonded iodine by weight in grain alcohol; and wherein the current density which is achieved is 30 amperes for 20 minutes.

2. The method of claim 1, wherein the pre-nascent iodine in solution which is produced becomes activated in the form of nascent iodine when diluted in water and consumed.

3. The method of claim 2, wherein the electrolytic bath is formulated by mixing ⅔ pounds of copper sulfate per gallon of bath, ½ ounces of sulfuric acid per gallon of bath, and ⅓ ounces of zinc chips per gallon of bath.

4. The method of claim 2, wherein anodes of copper and nickel alloy ½ inch in diameter and 14 inches in length are connected to an alternating current source and are inserted within the electrolytic bath.

* * * * *